United States Patent

Schödel et al.

[11] Patent Number: 5,820,829
[45] Date of Patent: Oct. 13, 1998

[54] HAND-OPERATED POLYMERIZER

[75] Inventors: Dieter Schödel, Wiesbaden; Steffen Oppawsky, Bad Homburg, both of Germany

[73] Assignee: Heraeus Kulzer GmbH, Hanau, Germany

[21] Appl. No.: 679,109

[22] Filed: Jul. 12, 1996

[30] Foreign Application Priority Data

Jul. 12, 1995 [DE] Germany .......... 195 25 366.3

[51] Int. Cl.$^6$ .............. H05B 1/00; H05B 3/42; H05B 11/00; C08F 19/00
[52] U.S. Cl. .......... 422/133; 422/134; 422/135; 219/227; 219/229; 219/217
[58] Field of Search ................. 219/227, 229, 219/230, 217; 422/133, 134, 135; 526/64, 281; 162/157; 264/211.12; 428/523; 528/272, 503

[56] References Cited

U.S. PATENT DOCUMENTS

| | | | |
|---|---|---|---|
| 4,924,070 | 5/1990 | Friedman | 219/346 |
| 5,147,204 | 9/1992 | Pattern et al. | 219/346 |
| 5,198,678 | 3/1993 | Oppawsky | 250/455.11 |

FOREIGN PATENT DOCUMENTS

| | | |
|---|---|---|
| 3411996 | 10/1985 | Germany . |
| 38 25 055 | 1/1990 | Germany . |
| 88 15 147.6 | 5/1990 | Germany . |
| 40 28 566 | 3/1992 | Germany . |
| WO 90/06092 | 6/1990 | WIPO . |

*Primary Examiner*—Lynette F. Smith
*Attorney, Agent, or Firm*—Frishauf, Holtz, Goodman, Langer & Chick, P.C.

[57] ABSTRACT

A hand-operated polymerizer for the polymerization of synthetic materials, such as dental plastics. The polymerizer has a housing in which a light source and a fan are disposed, and which includes a light-emitting opening for emitting the light generated by the light source. The housing contains openings for permitting cooling air to enter the housing and for allowing heated air to exit the housing. In order to prevent the operator of the polymerizer from being impaired by heated air when operating the polymerizer, at least one air-conducting member is provided, wherein the position of the air-conducting member is changeable relative to the housing.

6 Claims, 1 Drawing Sheet

Figure
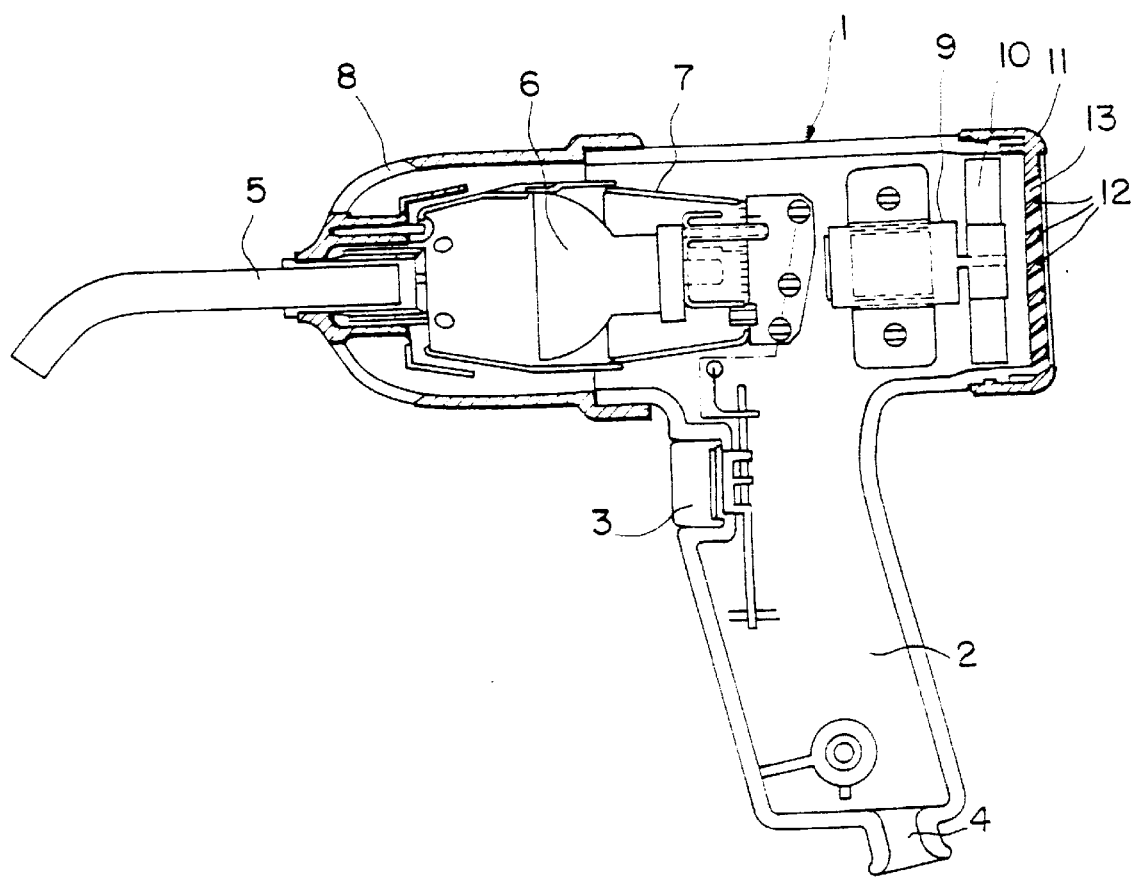

HAND-OPERATED POLYMERIZER

BACKGROUND OF THE INVENTION

1. Field of the Invention

The present invention pertains to a hand-operated polymerizer for the polymerization of synthetic materials, in particular dental plastics. The polymerizer has a housing containing a light source and a fan. The polymerizer has a light-releasing opening for emitting the light generated by the light source, as well as openings for allowing cooling air to enter and exit.

2. Background Information

A hand-operated polymerizer is described in DE 34 11 996 A1. The polymerizer of DE 34 11 996 A1 features a halogen reflector lamp wherein light is directed via a light conductor to the material to be polymerized. The light conductor is supported in the housing of the polymerizer.

A large portion of the energy used by the light source of DE 34 11 996 A1 is converted into thermal energy, which results in a heating-up of the housing. In order to prevent an excessive heating-up of the polymerizer and thus destruction of the entire device or sensitive parts of the device, the light source is cooled.

For the purpose of cooling the light source in DE 34 11 996 A1, openings are provided through which cooling air can enter the polymerizer from the outside and be directed to the light source, and can be returned back to the outside. The air flow is generated by a fan with a fan wheel. By means of the air flow, the heat generated by the light source is directed from the housing, so that on the one hand, destruction of the polymerizer by overheating is prevented and, on the other hand, the surface of the housing does not heat-up excessively. This is important, since at least a portion of the hand-operated polymerizer housing is designed, naturally, as a handle, with which the polymerizer is held and directed by an operator.

The direction of the hot air flow in DE 34 11 996 A1 is determined by the design of the outlet openings for the cooling air. These outlet openings are arranged at the front side of the rear housing portion which is slightly angled with respect to the remaining housing. When operating the polymerizer, the position of the polymerizer and therefore the outlet openings with respect to the operator can change, for example, during a polymerization procedure when various locations on a set of teeth of a patient require a corresponding change of position for the polymerizer. A different position for the outlet openings with respect to the body of the operator also results when the polymerizer is switched from the right hand to the left hand (for example, when a left-handed individual operates the polymerizer). Such a change of position also changes the outlet direction of the heated cooling air. In this context, it is possible that the hot air flow is oriented directly towards patients or operators. This is generally undesirable and can, in an extreme case, result in damage due to the influence of heat.

SUMMARY OF THE INVENTION

The present invention has the objective of providing a hand-operated polymerizer which can prevent the operator from being impaired by heated cooling air.

According to the present invention, the above objective is met by providing outlet openings for the cooling air, i.e., air-conducting members, which are arranged so as to be movable to alter their position with respect to the housing. As a result, the heated cooling air leaving the polymerizer can be guided in a direction where there are no persons or objects, so as to provide protection from the influence of heat. In this manner it is possible, for example, for the polymerizer to be used equally by right-handed, as well as left-handed individuals.

The present invention thus relates a hand-operated polymerizer for polymerizing a synthetic material comprising: a housing; a light source disposed in the housing; a light emitting opening disposed in front of the light source for receiving light from the light source and for emitting light generated by the light source to outside the housing; a fan disposed in the housing for cooling the light source; at least one air inlet opening disposed on the housing for permitting air to enter the housing; an air outlet member disposed on the housing for permitting air to exit the housing, the air outlet member having at least one air-conducting member, wherein the position of the at least one air-conducting member is changeable relative to the housing.

BRIEF DESCRIPTION OF THE DRAWING

For the purpose of illustrating the invention there is shown in the drawing an embodiment of the invention. It is to be understood, however, that the present invention is not limited to the precise arrangements and instrumentalities depicted in the drawing.

The sole drawing is a sectional view of a hand-operated polymerizer according to the present invention.

DETAILED DESCRIPTION OF THE INVENTION

Cooling air can exit the polymerizer through one or several outlet openings. What is of importance is the guiding of the direction of the exiting cooling air. It is suitable to dispose the air-conducting members at the end of the housing which is opposite the opening for emitting the light. It is particularly advantageous to arrange the air-conducting members obliquely to the longitudinal axis of the housing in order to guide the air flow out from the housing. That way, the direction of the cooling flow can be localized to a large extent.

It is expedient that several air-conducting members are arranged substantially parallel to each other; this makes it possible to guide the air flow relatively accurately.

For a simple system of movable air-conducting members, it is advantageous that the air-conducting members are arranged on a common frame, which is pivotally attached at the outlet opening for the cooling air. In particular, the air-conducting elements can be arranged in a rigid fashion on the frame. Based on such an arrangement of the air-conducting members, the cooling air flow can be guided through a simple rotation of the frame. Such an arrangement can be manufactured with a relatively high stability and at a reasonable cost. In order to optimally utilize the cooling air flowing through the housing, it is advantageous that the fan is disposed between the light source and the outlet openings for the cooling air.

The following is an exemplified embodiment of the invention which is explained in detail on the basis of the drawing.

The hand-operated polymerizer represented in the drawing includes a housing 1, which has an essentially cylindrical shape and at the underside thereof is molded a handle 2, with a switch 3 and an electrical connection 4.

One end (front end) of the cylindrical portion of the housing 1 has a light-releasing (light-emitting) opening, in which a light conductor 5 is arranged and which receives the light emitted from the light source 6 located in the housing 1 and transmits the light to the location to be illuminated. For this purpose, the light source 6 has associated therewith a reflector which is arranged inside the light source holder 7.

Air inlet openings 8 for cooling air are disposed in the housing 1 and adjacent to the light conductor 5. At the end of the light source holder 7, facing away from light conductor 5, a fan, consisting of a fan motor 9 and a fan wheel 10, is arranged in front of a second end (back end) of the cylindrical portion of the housing 1. Disposed on this second end is a frame, i.e., an air outlet member 11 in which the air-conducting members 12 are disposed. The air-conducting members 12 are designed as fins arranged obliquely to the longitudinal axis of the housing 1, between which the air outlet openings 13 are located.

The air outlet member 11 thus embraces the second end of the housing 1 and can be rotated on the housing 1 around the longitudinal axis of the housing 1. The air outlet member 11 with the air-conducting elements 12 can be manufactured in a cost-effective manner as an injection-molded part. By rotating the air outlet member 11, the cooling-air flow is directed to the air-conducting members 12 and then through the air outlet openings 13, in the desired direction. In that way, the operator, the patient or objects which must be protected from the influence of heat are prevented from being hit by the cooling-air flow. When changing the position of the hand-operated polymerizer, the direction of the cooling-air flow can correspondingly be adjusted by means of a simple rotating of the air outlet member 11.

Principally, it is also possible to attach the air-conducting members 12 pivotally, for example, as flaps on a movable or stationary frame (air outlet member 11). The number of the air-conducting members 12 can be varied; it is possible that one air-conducting member 12 may be sufficient. The number of air-outlet openings 13 is thus variable.

In the above described arrangement, the light source 6, which generates the heat, is arranged between the air inlet openings 8 and the outlet openings 13 in such a manner that the cooled air circulates around the light source holder 7 with the light source 6 in a uniform manner, so that the heat can be drawn-off in an optimal fashion.

It will be appreciated that the instant specification is set forth by way of illustration and not limitation, and that various modifications and changes may be made without departing from the spirit and scope of the present invention.

What is claimed is:

1. A hand-operated polymerizer for polymerizing a synthetic material, comprising:

a housing;

a light source disposed in the housing;

a light emitting member disposed in front of the light source for receiving light from the light source and for emitting light generated by the light source to outside of the housing;

a fan disposed in the housing for cooling the light source;

at least one air inlet opening disposed on the housing for permitting air to enter the housing; and an air outlet member disposed on the housing for permitting air to exit the housing, the air outlet member having at least one air-conducting member, wherein the air outlet member is rotatable attached to said outlet opening whereby the position of the at least one air-conducting member is changeable relative to the housing, thus providing for the changing of the direction of air exiting the housing, the at least one air-conducting member is disposed obliquely to the longitudinal axis of the housing, whereby directing air exiting the housing away from an operator of the polymerizer.

2. The hand-operated polymerizer according to claim 1, wherein said at least one air-conducting member is disposed at an end of the housing which is opposite to said light emitting member.

3. The hand-operated polymerizer according to claim 1, wherein a plurality of said air-conducting members are arranged substantially parallel to each other.

4. The hand-operated polymerizer according to claim 1, wherein:

an outlet opening is disposed at an end of the housing which is opposite to the light emitting member;

said air outlet member is coupled to said housing at said outlet opening.

5. The hand-operated polymerizer according to claim 1, wherein said at least one air-conducting member is rigidly attached to said air outlet member.

6. The hand-operated polymerizer according to claim 4, wherein said fan is disposed between the light source and said air outlet opening.

* * * * *